United States Patent
Chen et al.

(10) Patent No.: US 7,370,511 B1
(45) Date of Patent: May 13, 2008

(54) GAS SENSOR WITH ATTENUATED DRIFT CHARACTERISTIC

(75) Inventors: Ing-Shin Chen, Danbury, CT (US);
Frank Dimeo, Jr., Danbury, CT (US);
Philip S. H. Chen, Bethel, CT (US);
Jeffrey W. Neuner, Bethel, CT (US);
James Welch, Fairfield, CT (US);
Bryan Hendrix, Danbury, CT (US)

(73) Assignee: MST Technology GmbH (DE)

( * ) Notice: Subject to any disclaimer, the term of this patent is extended or adjusted under 35 U.S.C. 154(b) by 251 days.

(21) Appl. No.: 10/795,529

(22) Filed: Mar. 8, 2004

(51) Int. Cl.
*G01N 33/00* (2006.01)
(52) U.S. Cl. ........................ 73/23.2; 73/31.05
(58) Field of Classification Search ................. 73/23.2, 73/31.05
See application file for complete search history.

(56) References Cited

U.S. PATENT DOCUMENTS

| | | | |
|---|---|---|---|
| 4,324,761 A * | 4/1982 | Harris | .................... 422/98 |
| 6,006,582 A | 12/1999 | Bhandari et al. | |
| 6,265,222 B1 | 7/2001 | DiMeo et al. | |
| 6,596,236 B2 | 7/2003 | DiMeo et al. | |
| 2002/0154310 A1 | 10/2002 | DiMeo et al. | |
| 2002/0171839 A1 | 11/2002 | DiMeo et al. | |
| 2003/0153088 A1 | 8/2003 | DiMeo et al. | |

FOREIGN PATENT DOCUMENTS

DE 19536719 A1 * 4/1997 ................. 73/31.05

* cited by examiner

*Primary Examiner*—Daniel S. Larkin
(74) *Attorney, Agent, or Firm*—Steven J. Hultquist; Intellectual Property/Technology Law

(57) ABSTRACT

A sensor with an attenuated drift characteristic, including a layer structure in which a sensing layer has a layer of diffusional barrier material on at least one of its faces. The sensor may for example be constituted as a hydrogen gas sensor including a palladium/yttrium layer structure formed on a micro-hotplate base, with a chromium barrier layer between the yttrium layer and the micro-hotplate, and with a tantalum barrier layer between the yttrium layer and an overlying palladium protective layer. The gas sensor is useful for detection of a target gas in environments susceptible to generation or incursion of such gas, and achieves substantial (e.g., >90%) reduction of signal drift from the gas sensor in extended operation, relative to a corresponding gas sensor lacking the diffusional barrier structure of the invention.

50 Claims, 7 Drawing Sheets

GAS SENSOR WITH ATTENUATED DRIFT CHARACTERISTIC

GOVERNMENT RIGHTS IN INVENTION

Work related to the invention hereof was conducted in the performance of Department of Energy Contract No. DE-FC36-99GO10451. The Government has certain rights in the invention.

BACKGROUND OF THE INVENTION

1. Field of the Invention

The present invention relates generally to gas sensors with attenuated drift characteristics, and in a specific aspect to a hydrogen gas sensor including a palladium/yttrium layer structure, such as may be employed in environments susceptible to generation or incursion of hydrogen gas. More generally, the invention relates to a sensor with a sensing layer whose response to a target species is subject to drift in extended use.

2. Description of the Related Art

U.S. Pat. No. 6,006,582 issued Dec. 28, 1999 in the names of Gautam Bhandari, et al. for "Hydrogen Sensor Utilizing Rare Earth Metal Thin Film Detection Element," discloses a hydrogen sensor including a rare earth metal thin film arranged for exposure to the environment and exhibiting a detectable change of physical property, e.g., electrical conductance, electrical resistance, electrical capacitance, magnetoresistance, etc., when the rare earth metal thin film is contacted with hydrogen gas. The sensor is operatively coupled with an output assembly for converting the physical property change to a perceivable output in response to the presence of hydrogen in the monitored gas environment.

U.S. Pat. No. 6,265,222 issued Jul. 24, 2001 in the names of Frank DiMeo, Jr., et al. for "Micro-Machined Thin Film Hydrogen Gas Sensor, and Method of Making and Using the Same," discloses a hydrogen sensor including a thin film sensor element of similar type formed, e.g., by metalorganic chemical vapor deposition (MOCVD) or physical vapor deposition (PVD) of a hydrogen-interactive metal film on a micro-hotplate structure. The hydrogen-interactive metal film in a preferred embodiment is overcoated with a thin film hydrogen-permeable barrier layer to protect the hydrogen-interactive film from deleterious interaction with non-hydrogen species.

When micro-hotplate hydrogen gas sensors of the foregoing type are utilized with yttrium as the hydrogen-interactive metal film and palladium as the thin film hydrogen-permeable barrier layer to protect the yttrium film from interaction with non-hydrogen species, the performance of the sensor initially is highly effective, but degrades with time.

This progressive degradation is manifested as drift in the output signal derived from the sensor, and is of sufficient magnitude to seriously adversely impact the accuracy and service lifetime of the sensor. Drift rates well in excess of 5% per day have been documented for micro-hotplate hydrogen sensors having a Pd/Y bilayer structure formed on a silicon dioxide insulating layer mounted on aluminum contact pads. Such rates of degradation severely compromise the usefulness of the hydrogen sensor, requiring constant recalibration if the sensor is to used for extended in-service operation, and raising the possibility that significantly increased concentrations of hydrogen may be present in the monitored gas environment before detection occurs, relative to detection capability of the sensor at inception of use.

It would therefore be a significant advance in the art to provide a reliable hydrogen gas sensor structure that avoids the foregoing problems, and is characterized by a very low rate of drift in use.

SUMMARY OF THE INVENTION

The present invention relates generally to sensors with a sensing layer whose response to a target species is subject to drift in extended use, such as gas sensors for detection of target gas species, e.g., hydrogen, ammonia, sulfur-containing gases, etc.

In a specific embodiment, the invention relates to a hydrogen sensor including a palladium/yttrium layer structure, such as may be employed for $H_2$ detection in environments susceptible to generation or incursion of hydrogen or hydrogen-containing gas.

In one aspect, the invention relates to a sensor including a sensing layer producing a response in contact with a target species, wherein such response is indicative of presence of the target species in a locus monitored by the sensor, wherein the sensor includes at least one material adjacent to the sensing layer, and wherein the sensor includes a diffusional barrier layer between the sensing layer and the adjacent material.

In another aspect, the invention relates to gas sensor comprising:
   (a) a substrate, e.g., a micro-hotplate,
   (b) a target gas sensing layer overlying the substrate, and
   (c) optionally, a protective layer overlying the target gas sensing layer, permeable to the target gas and restricting contact of the target gas sensing layer with non-target gas species, wherein the gas sensor comprises at least one diffusional barrier layer between the target gas sensing layer and a layer adjacent thereto.

In yet another aspect, the invention relates to a gas sensor comprising
   (a) a micro-hotplate;
   (b) a target gas sensing layer overlying the micro-hotplate;
   (c) a protective layer overlying the target gas sensing layer, permeable to the target gas and restricting contact of the target gas sensing layer with non-target gas species;
   (d) a first diffusional barrier layer between the protective layer and the target gas sensing layer; and a second diffusional barrier layer between the target gas sensing layer and the micro-hotplate.

In a still further aspect, the invention relates to a hydrogen sensor, comprising:

at least one hydrogen-interactive thin film sensor element comprising a rare earth metal or a rare earth metal hydride;

at least one micro-hotplate structure coupled to said hydrogen-interactive sensor element for selective heating of the sensor element; and a hydrogen-permeable material overlaying each hydrogen-interactive sensor element for selective permeation of hydrogen, with a first diffusional barrier layer between said micro-hotplate structure and said hydrogen-interactive sensor element, and a second diffusional barrier layer between said hydrogen-interactive sensor element and said hydrogen-permeable material.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
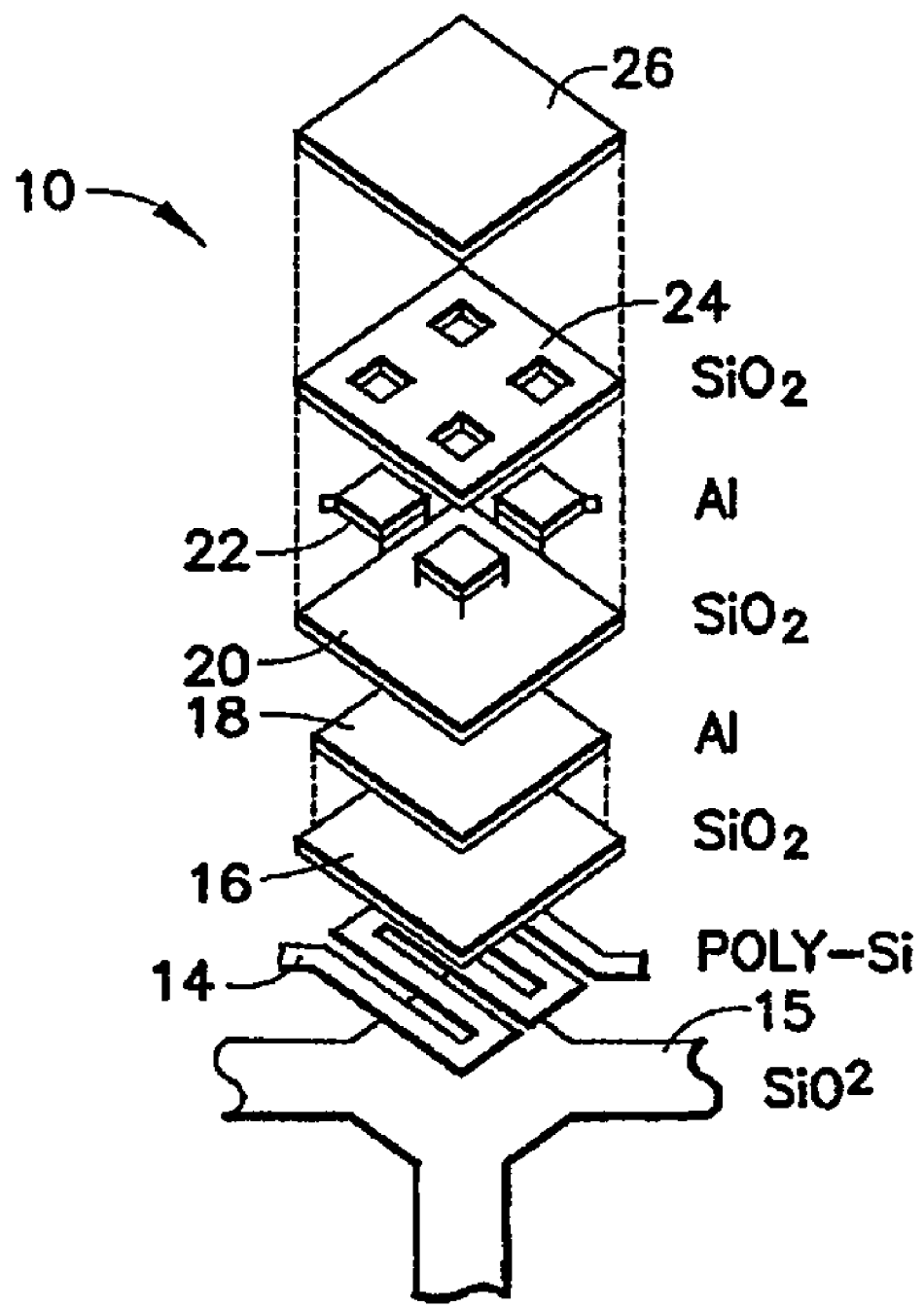
FIG. 1 is a schematic representation of a gas sensor according to one embodiment of the invention.

The contents of the following U.S. patents and U.S. patent publications and applications are hereby incorporated herein by reference in their respective entireties for all purposes: U.S. Pat. No. 6,596,236 issued Jul. 22, 2003 for "Micro-Machined Thin Film Sensor Arrays for the Detection of H$_2$ Containing Gases, and Method of Making and Using the Same;" U.S. Pat. No. 6,006,582 issued Dec. 28, 1999 for "Hydrogen Sensor Utilizing Rare Earth Metal Thin Film Detection Element;" U.S. Pat. No. 6,265,222 issued Jul. 24, 2001 for "Micro-Machined Thin Film Hydrogen Gas Sensor, and Method of Making and Using the Same;" U.S. Patent Application Publication No. US2002/0154310 A1 published Oct. 24, 2002 for "Optical Hydrogen Detector;" U.S. Patent Application Publication No. US2002/0171839 A1 published Nov. 21, 2002 for "Optical Hydrogen Detector;" U.S. Patent Application Publication No. US2002/0153088 A1 published Aug. 14, 2003 for "Micro-Machined Thin Film Sensor Arrays for the Detection of H2, NH3, and Sulfur Containing Gases, and Method of Making and Using the Same;" and U.S. patent application Ser. No. 10/429,909 filed May 5, 2003 for "Chemical Sensor Responsive to Change in Volume of Material Exposed to Target Particle."

The present invention is based on the discovery, involving micro-hotplate gas sensors but more generally applicable to other sensors, that the undesired drift characteristics of such sensors can be substantially and unexpectedly reduced by the interposition of a diffusional barrier layer between an active sensing layer and an adjacent layer of the sensor. This unexpected character of this discovery relates to the following factors:

(i) one of skill in the art would logically not attribute drift in the output response of the gas sensor to interfacial effects between adjacent layers in the sensor structure;

(ii) one of skill in the art would more logically attribute drift of the output response of the gas sensor to time-variant behavior in the signal processing module or other electronics associated with the gas sensor, or alternatively to complexation of the active gas species (hereafter referred as the "target gas," i.e., the gas species that the gas sensor is intended to detect in use) with impurities or materials of construction in the gas sensor; and (iii) one of skill in the art would logically anticipate that placement of a barrier material on a surface of the active gas sensing layer of the sensor would, if disposed on the surface adjacent to the micro-hotplate, attenuate the thermal responsivity of the gas sensor and render it unsatisfactory for its intended purpose, and that placement of a barrier material on a surface of the gas sensing layer adjacent to an overlying protective layer would provide a substantial impedance to flux of the target gas, and thereby unsatisfactorily reduce the detection response rate.

The present invention broadly contemplates a sensor including a sensing layer producing a response in contact with a target species (the species that the sensor is intended to detect in use), wherein such response is indicative of presence of the target species in a locus monitored by the sensor, wherein the sensor includes at least one material adjacent to the sensing layer, and wherein the sensor includes a diffusional barrier layer between the sensing layer and the adjacent material.

The sensor may be of any suitable type, including gas sensors, optical sensors, chemical sensors, piezo-resistive devices, etc., in which a sensing layer produces a response in contact with the target species. Examples of sensors and piezo-resistive devices are set out in the aforementioned U.S. patents, patent application publications and patent application identified and incorporated by reference herein.

The sensing layer can be of any suitable type that produces a useful response in contact with the target species. The response may for example include change in one or more physical, chemical, dimensional, electrical, optical, magnetic, ferroelectric, acoustic, or other properties, so that the response is able to be outputted, or otherwise employed to produce a useful result, such as actuating a switch, component or other element, effecting a change of state in an output medium, or providing a signal for signal processing operations. For example, resistance, resistivity, physical volume, strain, or other characteristic may be used to generate an output indicative of the presence of the target species in the environment being monitored by the sensor.

In the piezo-resistive device, for example, the sensing layer can include (i) a contacting layer that in exposure to the target species undergoes a change in volume, and (ii) a resistance layer contiguous to the contacting layer. The resistance layer in response to the expansion of the contacting layer undergoes a change in resistance, and this change in resistance in turn constitutes an output from the sensor that is indicative of the presence of the target species.

In a specific embodiment, wherein hydrogen is the target species, the piezo-resistive sensor can comprise an yttrium film as the contacting layer, overlying a polysilicon film constituting the resistance layer. The resistance change of the polysilicon film thus is monitored to determine presence of hydrogen in the monitored environment of the sensor.

The sensing layer in the sensor of the invention is adjacent to a material which differs from the composition of the sensing layer. Such material can be present in the form of a support or substrate for the sensing layer, or constitute some other structural member or body adjacent to the sensing layer. Examples of substrate materials for the sensing layer include glasses (e.g., quartz or silica-based glasses), metals, dielectric materials, semiconductors, etc.

The adjacent material may for example be in the form of a layer or sheet-form material, e.g., in a multi-layer structure in which the sensing layer is a component. The adjacent material in such a layer or sheet-form may for example constitute a protective material that is perm-selective for a target species with which the sensing layer is interactive to produce the response.

The invention in a preferred aspect embodies a gas sensor including the sensing layer as an active component interactive with one or more gas species in an environment or locus with which the sensing layer is in gas-monitoring relationship. In one preferred specific embodiment, the gas sensor includes as the adjacent material an adjacent thermal source material serving to achieve a desired thermal condition of the sensing layer in use of the sensor, e.g., in the form of a micro-hotplate structure over which the sensing layer is disposed.

Thus, while the invention is illustratively disclosed hereinafter with primary reference to a micro-hotplate gas sensor, it will be appreciated that the scope of the invention is not thus limited, but rather extends to and encompasses any device structure in which a sensing layer is present in adjacent relationship to a material and is subject to drift in extended operation of the device.

The present invention in a specific aspect contemplates a gas sensor comprising:

(d) a substrate, e.g., a micro-hotplate,
(e) a target gas sensing layer overlying the substrate, and
(f) optionally, a protective layer overlying the target gas sensing layer, permeable to the target gas and restricting contact of the target gas sensing layer with non-target gas species, wherein the gas sensor comprises at least one diffusional barrier layer between the target gas sensing layer and a layer adjacent thereto.

The diffusional barrier layer(s) can be formed of any suitable material that is different from the composition of either adjacent layer between which the diffusional barrier layer is interposed, which does not preclude the efficacy of either of such adjacent layers, and which is effective to retard the extent of diffusion of materials of the adjacent layers into one another, relative to a corresponding layer structure lacking such diffusional barrier layer.

The nature of the diffusional barrier layer will of course depend on the specific identity and characteristics of the materials in the adjacent layers, and specific suitable diffusional barrier layer materials may be readily determined based on the disclosure herein, within the skill of the art and without undue experimentation, by comparative Auger depth profiling determinations of corresponding layer structures with and without the diffusional barrier layer.

The diffusional barrier layer may therefore be present between the target gas sensing layer and the substrate (e.g., micro-hotplate structure) and/or between the target gas sensing layer and a protective layer overlying such target gas sensing layer, if such a protective layer is present. The protective layer is a layer that is permeable to the target gas species, but shields the target gas sensing layer by restraining non-target gas species from contact with the target gas sensing layer. In a specific embodiment, the gas sensor utilizes a protective layer, and diffusional barrier layers are interposed between the target gas sensing layer and a micro-hotplate structure, as well as between the target gas sensing layer and the protective layer.

The target gas sensing layer itself can be of any suitable material that in exposure to the target gas species is changed in a manner that permits the change to be used as the basis for a perceivable output from the sensor that is indicative of the presence of the target gas in the environment being monitored by the gas sensor.

While the invention is variously described hereinafter with primary reference to hydrogen gas sensors for purposes of illustration, it will be understood as encompassing other target gas species, and correspondingly other active gas sensing materials, protective materials and diffusional barrier materials, relative to those described hereinafter in connection with $H_2$ sensors.

In a specific embodiment, the invention contemplates a hydrogen sensor, comprising:

at least one hydrogen-interactive thin film sensor element comprising a rare earth metal or a rare earth metal hydride;
at least one micro-hotplate structure coupled to said hydrogen-interactive sensor element for selective heating of the sensor element; and
a hydrogen-permeable material overlaying each hydrogen-interactive sensor element for selective permeation of hydrogen,
with a first diffusional barrier layer between said micro-hotplate structure and said hydrogen-interactive sensor element, and
a second diffusional barrier layer between said hydrogen-interactive sensor element and said hydrogen-permeable material.

The gas sensor of the invention may be configured in a specific embodiment as a hydrogen gas sensor, including a hydrogen-interactive thin film element on a micro-hotplate structure. The hydrogen-interactive thin film sensor element of such sensor may comprise a hydrogen-interactive thin film (i) arranged for exposure to an environment susceptible to the incursion or generation of hydrogen and (ii) exhibiting a detectable change of physical property when the hydrogen-interactive thin film is exposed to hydrogen.

As used herein, the term "hydrogen-interactive thin film element" means one or more thin films wherein at least one thin film is selected from the group consisting of one or more rare earth metals, one or more Group II elements as well as alloys or combinations thereof. As used herein the term "rare earth metal" means a metal selected from scandium, yttrium, lanthanum, the lanthanides, and the actinides as well as alloys and combinations of such metals, and alloys and combinations of such metals with Group II elements, e.g., calcium, barium, strontium, magnesium and radium. The lanthanides are the fourteen elements following lanthanum in the Periodic Table, viz., cerium, praseodymium, neodymium, promethium, samarium, europium, gadolinium, terbium, dysprosium, holmium, erbium, thulium, ytterbium and lutetium. The actinides are the elements of the Periodic Table having the atomic numbers 89 through 103 inclusive, viz., actinium, thorium, protactinium, uranium, neptunium, plutonium, americium, curium, berkelium, californium, einsteinium, fermium, mendelevium, nobelium and lawrencium.

The detectable change of physical property of the gas sensing layer material can comprise optical transmissivity, electrical resistivity, electrical capacitance, magneto-resistance, photoconductivity, and/or any other detectable property change accompanying the exposure of the thin film sensor element to hydrogen. The hydrogen sensor may further include a detector constructed and arranged to convert the detectable change of physical property to a perceivable output, e.g., a visual output, auditory output, tactile output, and/or auditory output.

As discussed hereinabove, the hydrogen-interactive thin film as the target gas sensing layer can be overlaid by a protective layer. The protective layer for the hydrogen sensor can advantageously be constituted by a hydrogen-permeable material protecting the rare earth metal thin film from deleterious interaction with non-hydrogen components of the environment being monitored, such as nitrogen, oxygen, water, ammonia, hydrocarbons, etc.

The protective-over layer may include a metal such as Pd, Pt, Ir, Rh, Ag, Au, Co, and/or alloys thereof.

The gas sensing layer may be formed of a rare earth film material which is alloyed with one or more suitable elements, such as silver, titanium, nickel, chromium, aluminum or other species known to those skilled in the art. Alternatively, or additionally, the rare earth film material may be doped with a dopant species, such as for example magnesium, calcium, strontium, barium, or a combination thereof.

The micro-hotplate sensor of the invention can utilize a micro-hotplate structure that is constructed and arranged for selectively heating the hydrogen-interactive thin film gas sensor element (target gas sensing layer) according to a predetermined time-temperature program, e.g., involving cyclic heating of the hydrogen-interactive thin film gas sensor element by the micro-hotplate structure.

The gas sensor of the invention can be operatively arranged with a detector for sensing a detectable change of a physical or other property of the target gas sensing layer in exposure to the target gas and generating a correlative output indicative of presence of the target gas. A power supply may be provided and may be constructed and arranged for (i) actuating the micro-hotplate structure during and/or subsequent to sensing the detectable change of physical or other property of the target gas sensing layer in exposure to the target gas (e.g., a rare earth metal thin film in exposure to hydrogen), and/or (ii) energizing the detector.

The layers in the gas sensor may be formed in any suitable manner appropriate to the materials involved. Generally, the various layers in the layer structure of the gas sensor are formed as thin films, e.g., having a thickness of less than 1 micrometer, as for example in a range of from 5 nanometers to 0.5 micrometer, by any suitable thin film formation technique. Examples of thin film formation techniques that can be usefully employed in the broad practice of the invention include, without limitation, sputter deposition, e-beam deposition, solution deposition, metal-organic chemical vapor deposition (MOCVD), physical vapor deposition (PVD), and corresponding assisted vapor deposition processes, such as plasma-assisted MOCVD.

The micro-hotplate structure of the sensor device of the invention may be readily fabricated by micro-machining techniques, as for example based on complementary metal oxide semiconductor (CMOS) fabrication techniques.

The gas sensor of the invention is a solid-state device that may be adapted in a variety of apparatus embodiments to accommodate the objects of the invention.

In one embodiment, the gas sensor is arranged for detection of hydrogen gas, using selective heating of a sensor film by the micro-hotplate structure to increase the rate of interaction of the sensor film with any hydrogen gas in the environment being monitored, and to increase the rate of regeneration or recovery of the sensor film.

For such purpose, the micro-hotplate can be coupled with suitable power supply and cycle time controller circuitry, so that the micro-hotplate structure provides appropriate heating of the hydrogen-interactive sensor film for the desired monitoring operation. Such power supply and cycle time controller circuitry may for example be constructed and arranged for pulsed or variable cycle time operation, or according to a selected time-temperature schedule.

The gas sensing layer in hydrogen sensors in a specific aspect of the invention can be a hydrogen-interactive material thin film that is from about 50 to about 2000 nm thick, and more preferably from about 50 to about 200 nm thick, with a protective layer when present having a thickness of from about 2 to about 1000 nm, and more preferably from about 2 to about 100 nm, e.g., a 20 nm thick protective layer of a material such as Pd on an yttrium film of 100 nm thickness. The protective over layer is preferably thick enough to adequately protect the sensor from oxidation and thin enough to enable high responsivity of hydrogen sensing to be achieved in the operation of the device.

The diffusional barrier layers can be of any suitable thickness appropriate to the specific gas sensor in which the gas sensing layer is employed. By way of example, the bottom diffusional layer interposed between the micro-hotplate and the gas sensing layer may be on the order of from about 5 to about 200 nanometers in thickness, although greater or lesser thicknesses can be used to good effect in the broad practice of the invention, and the top diffusional layer interposed between the gas sensing layer and an overlying protective layer can likewise be of a thickness on the order of from about 5 to about 200 nanometers, although greater or lesser thicknesses can be employed in the general practice of the invention, depending on the thickness of the gas sensing layer and other layers in the multi-layer structure of the invention, the target gas species for which the gas sensing layer is effective, and the diffusivity, chemical character and other properties of the non-target gas(es) in the environment being monitored for the presence of the target gas.

The gas sensing layer and the overlying protective layer may be deposited on the substrate in any suitable manner, and the films may be hydrogenated, annealed and/or otherwise processed, as desirable to provide layers in the multi-layer gas sensing structure that have resistivity and other properties of the desired character.

The diffusional barrier layer between the micro-hotplate and the hydrogen sensing layer can be of any suitable material, such as a material including an element selected from the group consisting of elements of Group IIA excluding Be and Mg, elements of Group IIIB, IVB, VB, VIB, and lanthanide elements from Eu to Lu. The barrier diffusion layer between the hydrogen sensing layer and the protective overlayer, if present, preferably includes an element selected from the group consisting of V, Nb, Ta, Cr, Mo and W. More preferably, such barrier diffusion layer includes an element selected from among Cr, Mo and W.

In one embodiment, the barrier layer between the micro-hotplate and the hydrogen sensing layer is formed of chromium, e.g., at a thickness of 50 Angstroms, 75 Angstroms, 100 Angstroms, or other suitable thickness, in a hydrogen sensor including an yttrium layer of 2500 Angstroms thickness, with a protective palladium overlayer that is 250 Angstroms in thickness.

The chromium film in such embodiment may be deposited at the desired thickness, and the barrier film may be subjected to post-deposition processing including steps such as hydrogenation, e.g., in a 0.5% hydrogen and 99.5% nitrogen (percentages by volume) environment for 2040 minutes at temperature of 70-90° C., followed by annealing of the deposited film, e.g., at temperature on the order of 90-115° C. for 12-30 hours in ambient air or nitrogen environment. Hydrogenation is advantageous in such post-deposition processing to reduce the oxidation of the hydrogen sensing layer.

When an upper protective layer overlies the hydrogen sensing layer, the protective layer can be formed of a material including an element such as Pd, Pt, Ir, Rh, Ag, Au, or Co, or an alloy or combination of one or more of such elements, to enable hydrogen in the environment being monitored to pass readily through the protective layer while restricting passage of undesired gases such as nitrogen, oxygen, water, ammonia, hydrocarbons, carbon oxides, nitrogen oxides, and combinations of such non-target gases.

In such case, a diffusional barrier layer may be interposed between the hydrogen sensing layer and the protective overlayer to further restrict passage of undesired gases. The diffusional barrier layer can be formed of any suitable material, such as an element selected from the group consisting of elements of Group IIA excluding Be and Mg, elements of Group IIIB, IVB, VB, VIB, and lanthanide elements from Eu to Lu.

The barrier layer in one embodiment of the invention can include Tm or Lu. The barrier layer in another embodiment can include an element of Group VB of the Periodic Table. In one preferred embodiment, the barrier layer includes tantalum, deposited as an elemental film of such material, e.g., at a thickness of 50 Angstroms, 100 Angstroms or other suitable thickness. The barrier film may be subjected to post-deposition processing including steps such as hydrogenation, e.g., in a 0.5% hydrogen and 99.5% nitrogen (percentages by volume) environment for 20-40 minutes at temperature of 70-90° C., followed by annealing of the deposited film, e.g., at temperature on the order of 90-115° C. for 12-30 hours in ambient air or nitrogen environment. Hydrogenation is advantageous in such post-deposition processing to reduce the oxidation of the hydrogen sensing layer.

In a further embodiment, the barrier layer between the hydrogen sensing layer and the overlying protective layer includes alumina.

The barrier layer between the gas sensing layer and the protective overlayer must be permeable to the target gas, so that the target gas passes through the protective overlayer and intermediate diffusional barrier layer to contact the gas sensing layer for sensing of the target gas in the environment being monitored.

Referring now to the drawings, FIG. 1 is a schematic representation of a gas sensor according to one embodiment of the invention, in exploded view showing the constituent layers of a hydrogen sensor 10, as constructed according to one embodiment of the present invention.

The lowermost layer 15 is formed of silicon dioxide (SiO$_2$) and defines a suspended membrane or micro bridge. The next succeeding layers include polycrystalline silicon (Poly-Si) heating element 14, silicon dioxide insulating layer 16, conductive heat distribution plate 18 formed of aluminum, silicon dioxide insulating layer 20, four aluminum contact pads 22, and silicon dioxide insulating layer 24 with four openings therein communicating respectively with the four aluminum contact pads 22. The layers 15, 14, 16, 18, 20, 22 and 24 corporately constitute the micro-hotplate structure of the hydrogen sensor.

Overlying the silicon dioxide insulating layer 24 is the multilayer sensing unit 26. The multilayer sensing unit 26 may be constituted in any of the following variant structures, wherein the layers in the multilayer structure are identified beginning with the bottom layer and progressing successively and upwardly to the top layer:

multilayer sensing unit, variant I: a bottom diffusional barrier layer, overlaid by a target gas sensing layer, overlaid by a protective layer;

multilayer sensing unit, variant II: a bottom target gas sensing layer, overlaid by a diffusional barrier layer, overlaid by a top protective layer; or multilayer sensing unit, variant III: a bottom (first) diffusional barrier layer, overlaid by a target gas sensing layer, overlaid by a second diffusional barrier layer, overlaid by a protective layer.

Figure 2:
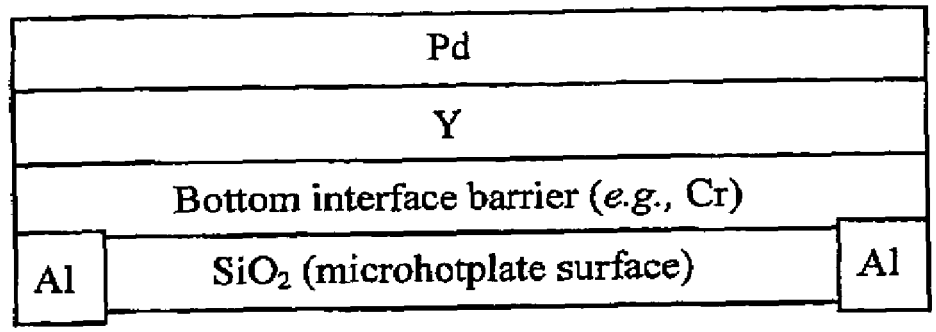
FIG. 2 is a schematic representation of a layer structure employed in a gas sensor of the general type shown in FIG. 1.

The multilayer sensing unit structure 26 may be of variant I type, as schematically shown in FIG. 2, for a structure including the micro-hotplate SiO$_2$ layer flanked by aluminum contact pads (Al), overlying which is a bottom interface layer of diffusional barrier material, such as chromium (Cr), overlying which is the target gas sensing layer of yttrium (Y), overlying which is the protective layer of palladium (Pd).

Figure 3:
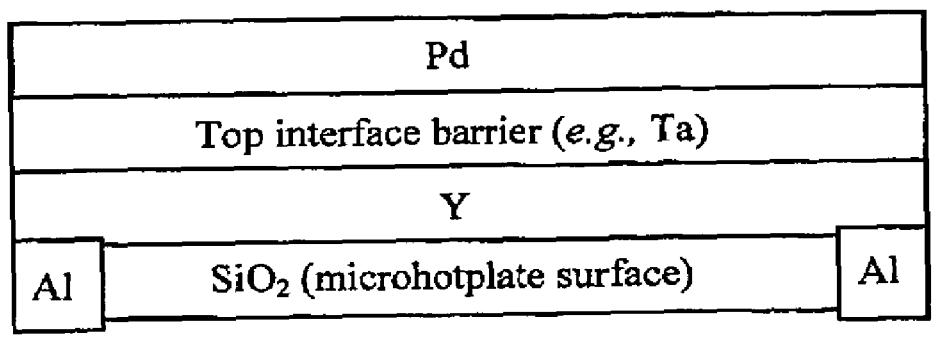
FIG. 3 is a schematic representation of another layer structure employed in a gas sensor of the general type shown in FIG. 1.

The multilayer sensing unit structure 26 alternatively may be of variant II type, as schematically shown in FIG. 3, for a structure including the micro-hotplate SiO$_2$ layer flanked by aluminum contact pads (Al), overlying which is the target gas sensing layer of yttrium (Y), overlying which is a top interface layer of diffusional barrier material, such as tantalum (Ta), overlying which is the protective layer of palladium (Pd).

Figure 4:
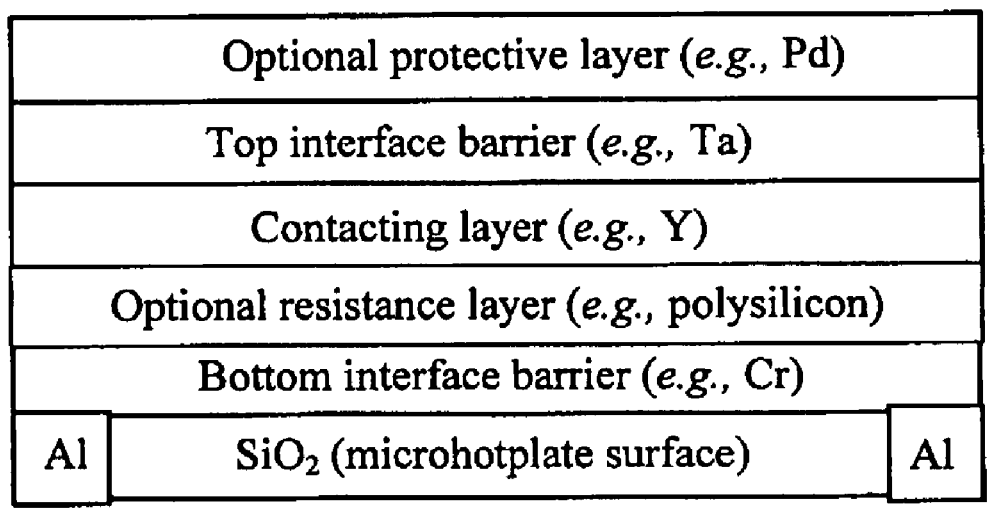
FIG. 4 is a schematic representation of yet another layer structure employed in a gas sensor of the general type shown in FIG. 1.

The multilayer sensing unit structure 26 as a still further variant may be of variant III type, as schematically shown in FIG. 4, for a structure including the micro-hotplate SiO$_2$ layer flanked by aluminum contact pads (Al), overlying which is a bottom interface layer of diffusional barrier material, such as chromium (Cr), overlying which is an optional resistance layer. e.g. of polysilicon, overlying which is the target gas sensing layer (contacting layer), e.g., of yttrium (Y), overlying which is a top interface layer of diffusional barrier material, such as tantalum (Ta), overlying which is an optional protective layer, of palladium (Pd).

The advantages of the invention are illustrated by the Auger depth profiling plots of composition shown in FIGS. 5-8.

Figure 5:
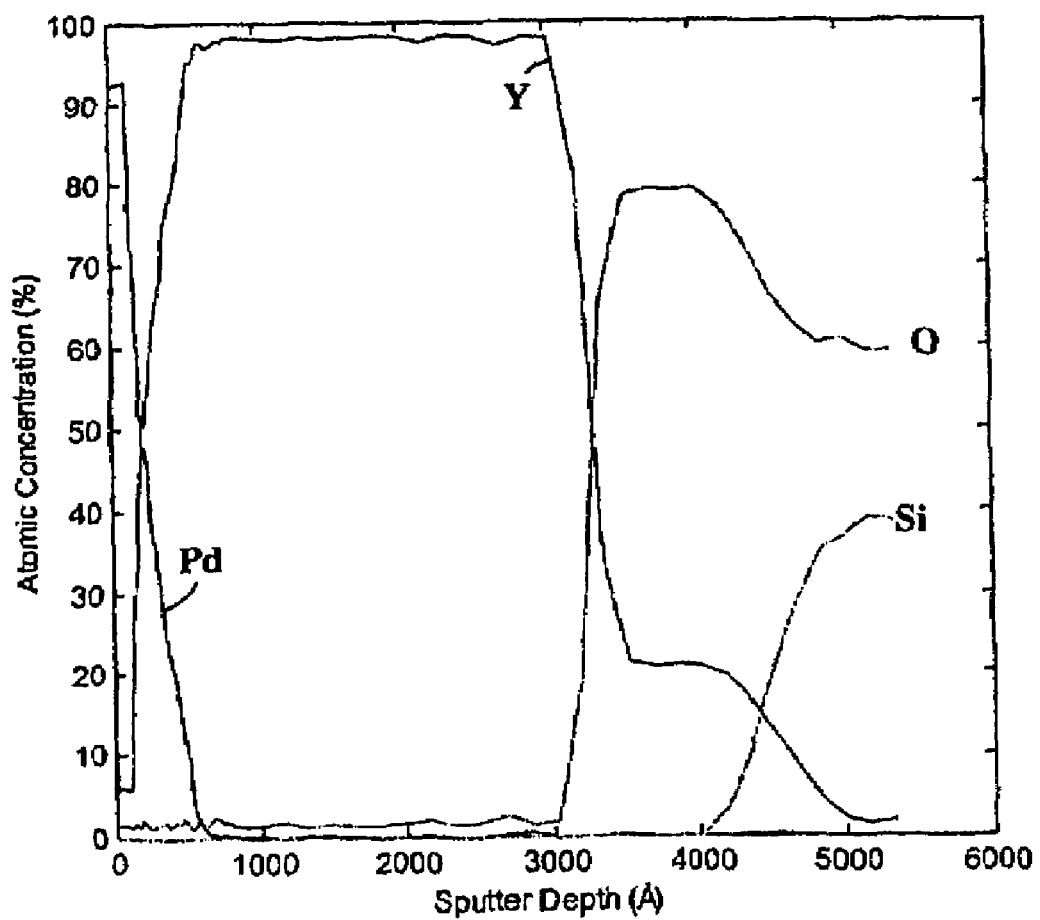
FIG. 5 (PRIOR ART) is an Auger depth profiling plot of composition, in atomic %, as a function of sputter depth, in nanometers, for a gas sensor Pd/Y/SiO$_2$ layer structure held at room temperature, after one month.

FIG. 5 is an Auger depth profiling plot of composition, in atomic %, as a function of sputter depth, in nanometers, for a gas sensor Pd/Y/SiO$_2$ layer structure held at room temperature, after one month.

Figure 6:
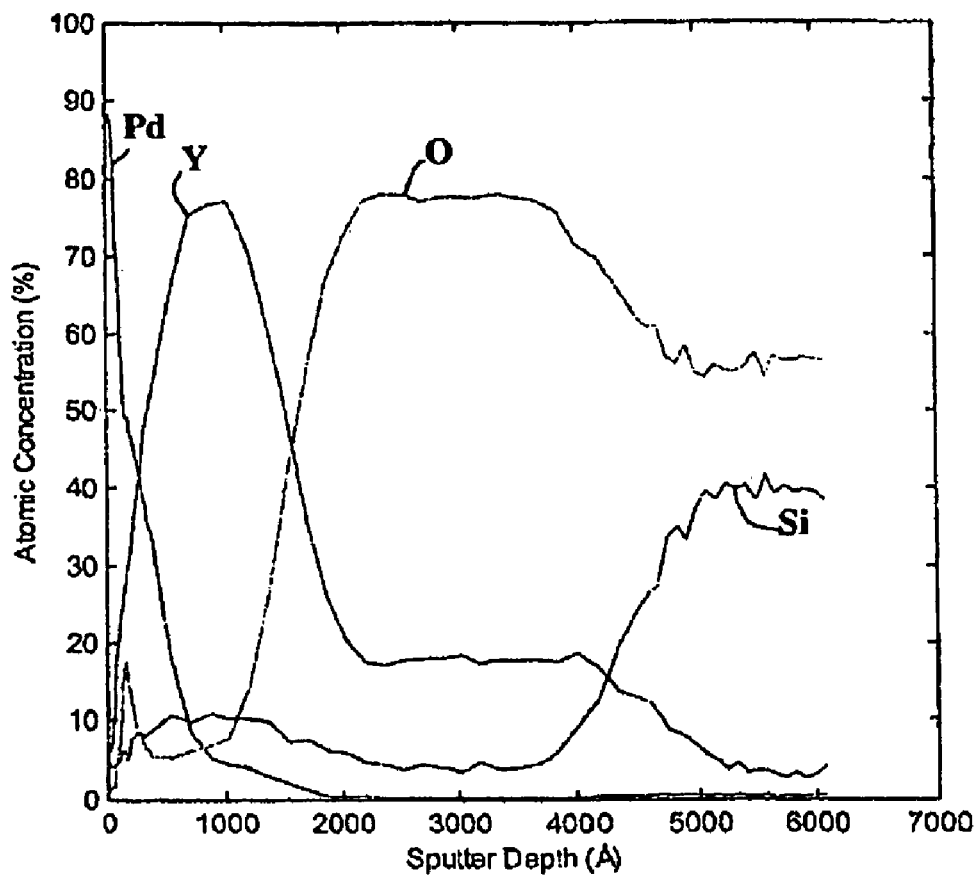
FIG. 6 (PRIOR ART) is an Auger depth profiling plot of composition, in atomic %, as a function of sputter depth, in nanometers, for a gas sensor Pd/Y/SiO$_2$ layer structure held at room temperature, after six months.

FIG. 6 is an Auger depth profiling plot of composition, in atomic %, as a function of sputter depth, in nanometers, for a gas sensor Pd/Y/SiO$_2$ layer structure held at room temperature, after six months.

The gas sensor for which data is shown in FIGS. 5 and 6 did not employ any diffusional barrier layers on either side of the yttrium layer. The Auger plots show concentration of oxygen (O), silicon (Si), yttrium (Y) and palladium (Pd), in atomic %, as a function of sputter depth of the multilayer film structure.

The curves shown in FIG. 5 evidence a surprising extent of diffusion of oxygen (O) into the target gas sensing layer of yttrium (Y), at the interface of the yttrium layer with the silicon dioxide layer ($SiO_2$) of the underlying micro-hotplate, after one month. In addition, in FIG. 6, the oxygen peak after six months at the top interface of the yttrium layer with the palladium layer evidences a significant presence of oxygen deriving from the ambient air environment of the sensor, and the substantial concentration of oxygen at the bottom interface of the yttrium layer with the silicon dioxide layer ($SiO_2$) of the underlying micro-hotplate evidences significant diffusion of oxygen from the silicon dioxide layer into the yttrium layer.

In addition, the Auger plots of FIGS. 5 and 6 show a significant interdiffusion of palladium and yttrium, which is undesirable from the perspective of maximizing the protective function of the palladium layer (isolating the yttrium sensing layer by the original overlying thickness of the palladium layer). Such diffusion may be exacerbated by elevated temperature conditions employed during fabrication of the multilayer gas sensing structure.

The concentration profiles of FIGS. 5 and 6 therefore evidence a basis for time-varying degradation of the gas sensing ability of the sensor for the target gas.

Figure 7:
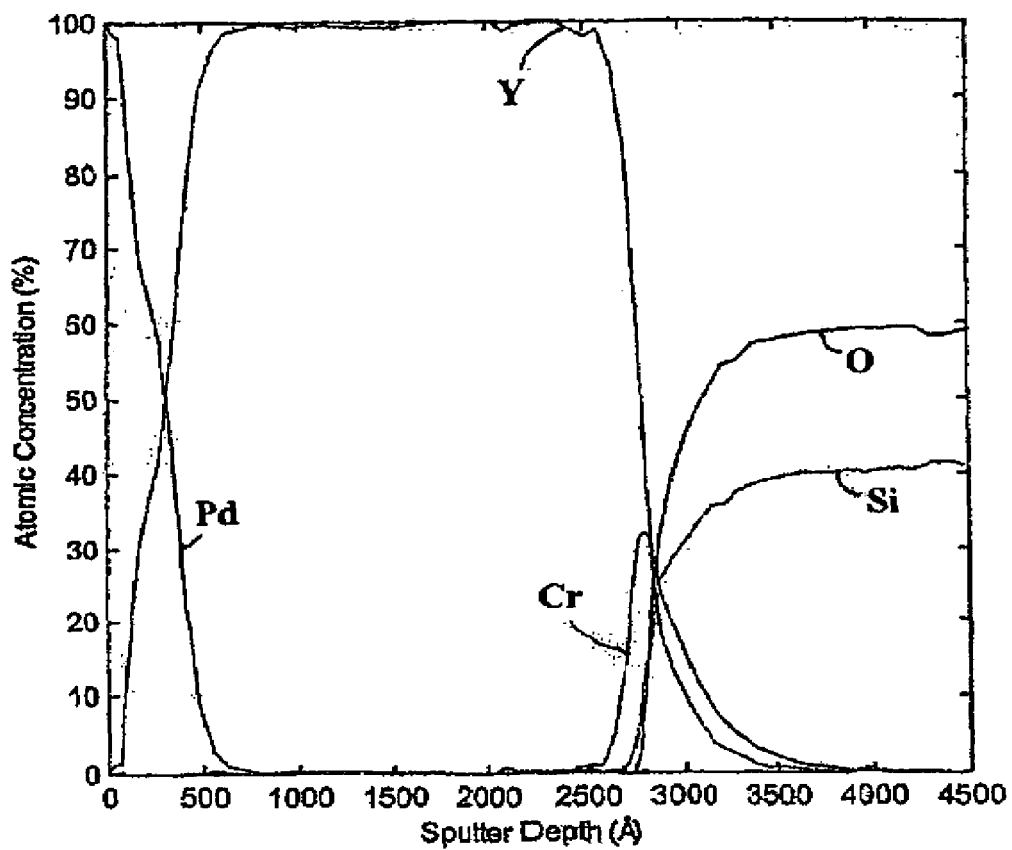
FIG. 7 is an Auger depth profiling plot of composition, in atomic %, as a function of sputter depth, in nanometers, for a gas sensor Pd/Y/Cr/SiO$_2$ layer structure, after twenty-four hours of annealing at approximately 100° C.

FIG. 7 is an Auger depth profiling plot of composition, in atomic %, as a function of sputter depth, in nanometers, for a gas sensor $Pd/Y/Cr/SiO_2$ layer structure in accordance with one embodiment of the present invention, after twenty-four hours of annealing at approximately 100° C.

The concentration curves shown in FIG. 7 illustrate the efficacy of a chromium bottom interfacial layer between the yttrium gas sensing layer and the $SiO_2$ micro-hotplate upper surface layer. As is apparent from a comparison of the Auger plot of FIG. 7 with the Auger plots of FIGS. 5 and 6, the presence of the interposed Cr layer intermediate the Y and $SiO_2$ layers in the layer structure whose compositional profiles are shown in FIG. 7 effects a substantial reduction of the amount of yttrium diffusion into the $SiO_2$ layer as well as in the amounts of diffusion of silicon and oxygen from the $SiO_2$ layer into the yttrium layer. The chromium interlayer in the structure for FIG. 7 therefore is shown to be an effective diffusional barrier layer when disposed between the micro-hotplate and the gas sensing layer.

Figure 8:
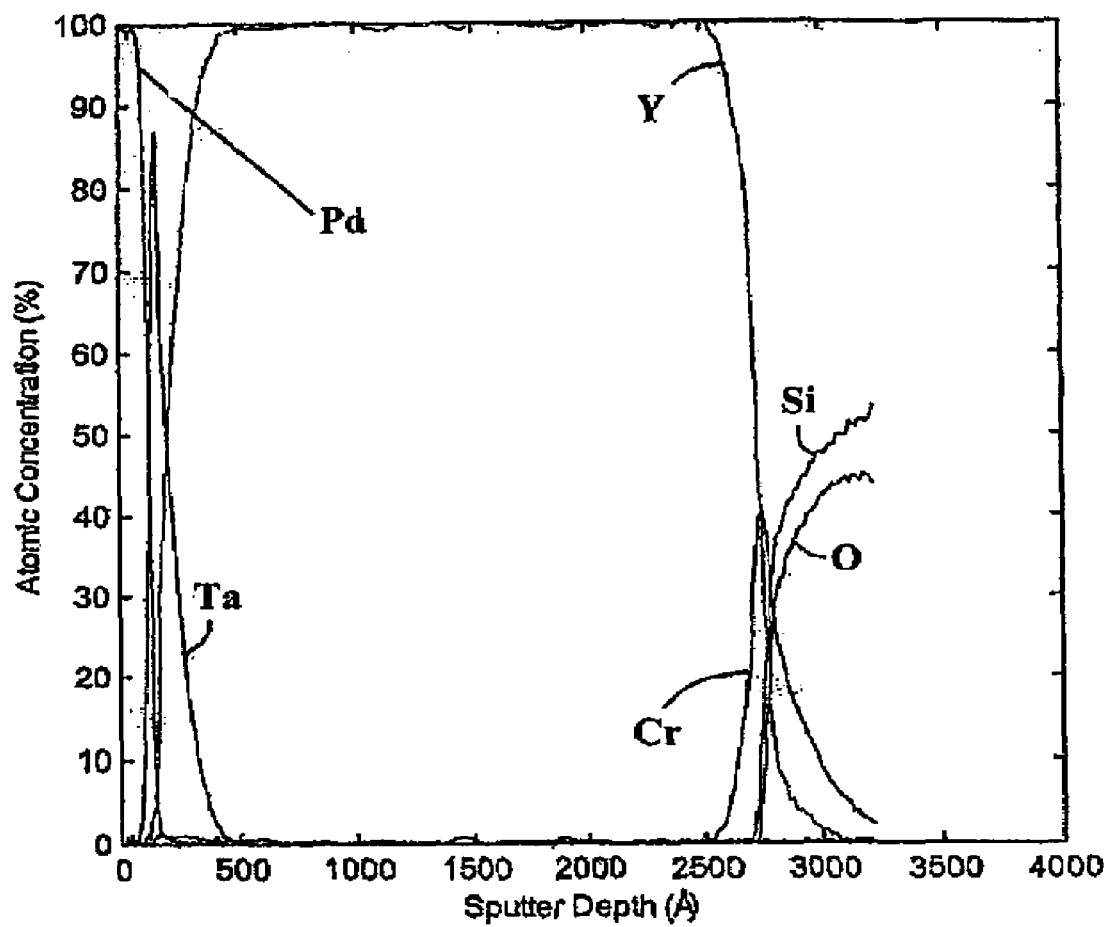
FIG. 8 is an Auger depth profiling plot of composition, in atomic %, as a function of sputter depth, in nanometers, for a gas sensor Pd/Ta/Y/Cr/SiO$_2$ layer structure, after twenty-four hours of annealing at approximately 100° C.

FIG. 8 is an Auger depth profiling plot of composition, in atomic %, as a function of sputter depth, in nanometers, for a gas sensor $Pd/Ta/Y/Cr/SiO_2$ layer structure, after twenty-four hours of annealing at approximately 100° C.

The FIG. 8 plot shows the same behavior by the Cr bottom diffusional barrier layer as in FIG. 7, with respect to the restriction of interdiffusion of yttrium and silicon/oxygen species at the interface of the yttrium gas sensing layer and the micro-hotplate.

Additionally, the FIG. 8 plot shows that the top interfacial barrier layer of tantalum interposed between the yttrium gas sensing layer and the overlying palladium protective layer is highly effective in suppressing the interdiffusion of yttrium and palladium (cf. FIG. 7).

The provision of top and bottom interfacial layers on the gas sensing layer therefore are effective to maintain the gas sensing layer at a substantially higher level of compositional homogeneity, relative to a corresponding gas sensing layer lacking such diffusional barrier layers.

As a result of the above-discussed compositional homogeneity at the interfacial regions of the gas sensing layer, the layer structure of the invention enables a remarkable improvement in stability of the gas sensing layer and the ability of the gas sensor incorporating same to operate for substantial periods of operation without the necessity of recalibration.

The invention therefore embodies a substantial advance in the art of gas sensing devices, by the provision of a reliable gas sensor structure characterized by a very low rate of drift in use, utilizing diffusional barrier layers in a gas sensing layer structure that is readily fabricated using thin film fabrication techniques.

Although the invention has been variously described herein with reference to illustrative embodiments and features, it will be appreciated that the embodiments and features described hereinabove are not intended to limit the invention, and that other variations, modifications and other embodiments will readily suggest themselves to those of ordinary skill in the art, based on the disclosure herein. The invention therefore is to be broadly construed, consistent with the claims hereafter set forth.

What is claimed is:

1. A sensor including a sensing layer producing a response in contact with a target species, wherein such response is indicative of presence of the target species in a locus monitored by the sensor, wherein the sensor includes at least one material adjacent to the sensing layer, and wherein the sensor includes a diffusional barrier layer between the sensing layer and the adjacent material, wherein the sensor constitutes a piezo-resistive device.

2. The sensor of claim 1, wherein the adjacent material comprises a substrate for the sensing layer.

3. The sensor of claim 2, wherein the substrate is formed of a material selected from the group consisting of glasses, metals, dielectric materials and semiconductors.

4. The sensor of claim 1, wherein the adjacent material is in a form of a layer.

5. The sensor of claim 1, constituting an optical sensor.

6. The sensor of claim 1, wherein the sensing layer includes (i) a contacting layer that in exposure to the target species undergoes a change in volume, and (ii) a resistance layer contiguous to the contacting layer, wherein the resistance layer undergoes a change in resistance upon change of volume of the contacting layer, with the change in resistance of the resisting layer constituting said response indicative of the presence of the target species.

7. The sensor of claim 6, wherein the contacting layer comprises an yttrium film and the resistance layer comprises a polysilicon film.

8. A gas sensor comprising:
   (a) a substrate, and
   (b) a target gas sensing layer overlying the substrate,
wherein the gas sensor comprises at least one diffusional barrier layer between the target gas sensing layer and a layer adjacent thereto;
wherein the target gas sensing layer does not contain titanium; and
wherein when the gas sensor includes a protective layer overlying the target gas sensing layer, permeable to the target gas and restricting contact of the target gas sensing layer with non-target gas species with which the sensing layer would otherwise be interactive, said at least one diffusional barrier layer between the target gas sensing layer and the layer adjacent thereto comprises at least one diffusional barrier layer between the target gas sensing layer and said protective layer, and said at least one diffusional barrier layer comprises an element selected from the group consisting of elements of Group IIIB, IVB, VB and VIB and lanthanide elements Eu and Tb to Lu.

9. The gas sensor of claim 8, wherein the gas sensor does not comprise a protective layer (c) overlying the target gas sensing layer.

10. The gas sensor of claim 8, further comprising a protective layer (c) overlying the target gas sensing layer, permeable to the target gas and restricting contact of the target gas sensing layer with non-target gas species.

11. The gas sensor of claim 10, wherein the gas sensor comprises said diffusional barrier layer between the target gas sensing layer and the substrate.

12. The gas sensor of claim 10, wherein the gas sensor comprises said diffusional barrier layer between the target gas sensing layer and the protective layer (c).

13. The gas sensor of claim 10, wherein the gas sensor comprises a first diffusional barrier layer between the target gas sensing layer and the substrate, and a second diffusional barrier layer between the target gas sensing layer and the protective layer (c).

14. The gas sensor of claim 8, wherein the target gas for which the target gas sensing layer is effective comprises hydrogen.

15. The gas sensor of claim 14, wherein the non-target gas species for which the protective layer is effective comprises a gas selected from the group consisting of nitrogen, oxygen, water, ammonia, hydrocarbons, carbon oxides, nitrogen oxides, and mixtures of the foregoing.

16. The gas sensor of claim 8, wherein the target gas sensing layer comprises a material selected from the group consisting of rare earth metals, Group II elements, and alloys and combinations thereof.

17. The gas sensor of claim 16, wherein the target gas sensing layer comprises a rare earth metal.

18. The gas sensor of claim 8, wherein the target gas sensing layer comprises a material selected from the group consisting of scandium, yttrium, lanthanum, the lanthanides, the actinides, and alloys and combinations thereof.

19. The gas sensor of claim 8, wherein the target gas sensing layer comprises yttrium.

20. The gas sensor of claim 7, further comprising a protective layer (c) overlying the target gas sensing layer, permeable to the target gas and restricting contact of the target gas sensing layer with non-target gas species, wherein the protective layer comprises a material selected from the group consisting of Pd, Pt, Ir, Rh, Ag, Au, Co, and alloys and combinations thereof.

21. The gas sensor of claim 8, wherein the at least one barrier diffusion layer comprises a barrier diffusion layer between the substrate and the target gas sensing layer, wherein the barrier diffusion layer comprises an element selected from the group consisting of elements of Group IIA excluding Be and Mg, elements of Group IIIB, IVB, VB, VIB, and lanthanide elements from Eu to Lu.

22. The gas sensor of claim 21, wherein the barrier diffusion layer comprises an element selected from the group consisting of V, Nb, Ta, Cr, Mo and W.

23. The gas sensor of claim 21, wherein the barrier diffusion layer comprises an element selected from the group consisting of Cr, Mo and W.

24. The gas sensor of claim 8, further comprising a protective layer (c) overlying the target gas sensing layer, permeable to the target gas and restricting contact of the target gas sensing layer with non-target gas species, wherein the at least one barrier diffusion layer comprises a barrier diffusion layer between the target gas sensing layer and the protective layer, wherein the barrier diffusion layer comprises an element selected from the group consisting of elements of Group VB, VIB, and lanthanide elements from Tb to Lu.

25. The gas sensor of claim 24, wherein the barrier diffusion layer comprises an element selected from the group consisting of Tm and Lu.

26. The gas sensor of claim 24, wherein the barrier diffusion layer comprises an element selected from the group consisting of Group VB.

27. The gas sensor of claim 24, wherein the barrier diffusion layer comprises Ta.

28. The gas sensor of claim 8, wherein the barrier diffusion layer comprises alumina.

29. The gas sensor of claim 8, wherein the substrate comprises a micro-hotplate.

30. A gas sensor comprising
(a) a micro-hotplate;
(b) a target gas sensing layer overlying the micro-hotplate;
(c) a protective layer overlying the target gas sensing layer, permeable to the target gas and restricting contact of the target gas sensing layer with non-target gas species;
(d) a first diffusional barrier layer between the protective layer and the target gas sensing layer, and
(e) a second diffusional barrier layer between the target gas sensing layer and the micro-hotplate.

31. The gas sensor of claim 30, wherein the target gas sensing layer comprises yttrium, the protective layer comprises palladium, the micro-hotplate comprises an upper surface including silicon dioxide, the first diffusional barrier layer comprises a Group VB element, and the second diffusional barrier layer comprises an element selected from the group consisting of Cr, Mo and W.

32. The gas sensor of claim 31, wherein the first diffusional barrier layer comprises chromium, and the second diffusional barrier layer comprises tantalum.

33. A hydrogen sensor, comprising:
at least one hydrogen-interactive thin film sensor element comprising a rare earth metal or a rare earth metal hydride;
at least one micro-hotplate structure coupled to said hydrogen-interactive sensor element for selective heating of the sensor element; and
a hydrogen-permeable material overlaying each hydrogen-interactive sensor element for selective permeation of hydrogen,
with a first diffusional barrier layer between said micro-hotplate structure and said hydrogen-interactive sensor element, and
a second diffusional barrier layer between said hydrogen-interactive sensor element and said hydrogen-permeable material.

34. The hydrogen sensor of claim 33, wherein the rare earth metal or rare earth metal hydride of the hydrogen-interactive sensor element comprises at least one rare earth metal component selected from the group consisting of trivalent rare earth metals that react with hydrogen to form at least two metal hydrides reaction products, wherein the two metal hydrides reaction products have differing physical properties.

35. The hydrogen sensor of claim 33, wherein the hydrogen-interactive thin film sensor element comprises at least one thin film layer comprising one or more metals, present in elemental metal form and/or in a hydride thereof, wherein the metal is selected from the group consisting of:

magnesium, calcium, strontium, barium, scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, lawrencium, and alloys thereof.

36. The hydrogen sensor of claim 33, further including a monitor operatively arranged in monitoring relationship to the hydrogen-interactive thin film sensor element to provide an output indicative of the presence of hydrogen.

37. The hydrogen sensor of claim 33, further including an electrical resistance monitor operatively arranged in monitoring relationship to the hydrogen-interactive thin film sensor element to provide an output indicative of the presence of hydrogen in an environment in contact with the hydrogen-interactive thin film sensor element.

38. The hydrogen sensor of claim 33, wherein the hydrogen-interactive thin film sensor element is formed of a material consisting essentially of rare earth metal hydride of one or more trivalent rare earth metals, wherein said rare earth metal hydride is reversibly reactive with hydrogen to form a corresponding second metal hydride exhibiting a detectable change of physical properties.

39. The hydrogen sensor of claim 33, wherein the hydrogen-permeable material is selected from the group consisting of palladium, platinum, iridium, silver, gold, cobalt, and alloys thereof.

40. The hydrogen sensor of claim 33, wherein the microhotplate structure is controlled by a predetermined time-temperature program for cyclic heating of the hydrogen-interactive thin film gas sensor element by the microhotplate structure.

41. The hydrogen sensor of claim 33, wherein said hydrogen-interactive thin film has a thickness of from about 50 to about 2000 nm.

42. The hydrogen sensor of claim 33, wherein the hydrogen-permeable material is in the form of a thin film.

43. The hydrogen sensor of claim 42, wherein the hydrogen-permeable thin film has a thickness of from about 2 to about 1000 nm.

44. The hydrogen sensor of claim 33, wherein the hydrogen-interactive thin film sensor element comprises a rare earth metal thin film that is doped with a dopant.

45. The hydrogen sensor of claim 44, wherein said dopant is selected from the group consisting of magnesium, calcium, strontium, barium, and any combination thereof.

46. The hydrogen sensor of claim 33, wherein the rare earth metal or rare earth metal hydride of the hydrogen-interactive sensor element, arranged for exposure to an environment susceptible to the incursion or generation of hydrogen exhibits a detectable change of property when exposed to hydrogen.

47. The hydrogen sensor of claim 46, wherein said detectable change of property includes a change in at least one property selected from the group consisting of optical transmissivity, physical volume, strain, electrical resistivity, electrical conductivity, electrical capacitance, magneto-resistance and photoconductivity.

48. The hydrogen sensor of claim 46, further comprising a detector constructed and arranged to convert said detectable change of property to a perceivable output selected from the group consisting of visual outputs, auditory outputs, tactile outputs, and auditory outputs.

49. The hydrogen sensor of claim 46, wherein said detectable change of property comprises a change of electrical property when the hydrogen-interactive thin film sensor element is contacted with hydrogen gas.

50. The hydrogen sensor of claim 46, wherein the hydrogen-interactive thin film sensor element comprises yttrium, and the physical property change comprises a change of electrical conductivity or resistivity when the hydrogen-interactive thin film sensor element is contacted with hydrogen gas.

* * * * *